US007923458B2

(12) United States Patent
Tabakoff

(10) Patent No.: US 7,923,458 B2
(45) Date of Patent: *Apr. 12, 2011

(54) METHOD FOR TREATING CHRONIC PAIN

(75) Inventor: Boris Tabakoff, Elizabeth, IL (US)

(73) Assignee: Lohocla Research Corporation, Aurora, CO (US)

( * ) Notice: Subject to any disclaimer, the term of this patent is extended or adjusted under 35 U.S.C. 154(b) by 261 days.

This patent is subject to a terminal disclaimer.

(21) Appl. No.: 12/083,110

(22) PCT Filed: Oct. 6, 2006

(86) PCT No.: PCT/US2006/039424
§ 371 (c)(1),
(2), (4) Date: Apr. 4, 2008

(87) PCT Pub. No.: WO2007/044682
PCT Pub. Date: Apr. 19, 2007

(65) Prior Publication Data
US 2009/0137627 A1    May 28, 2009

Related U.S. Application Data

(60) Provisional application No. 60/724,540, filed on Oct. 7, 2005.

(51) Int. Cl.
*A01N 43/42* (2006.01)
*A61K 31/47* (2006.01)
(52) U.S. Cl. ........................................ 514/312; 514/313
(58) Field of Classification Search .................. 514/312
See application file for complete search history.

(56) References Cited

U.S. PATENT DOCUMENTS 6,962,930 B1 * 11/2005 Tabakoff et al. .............. 514/313
* cited by examiner

*Primary Examiner* — Sreeni Padmanabhan
*Assistant Examiner* — Timothy E Betton
(74) *Attorney, Agent, or Firm* — Olson & Cepuritis, Ltd.

(57) ABSTRACT

A method for the treatment of chronic pain in a mammal is provided. The method comprises administering to a mammal (e.g., a human) suffering from chronic pain a pain relieving amount of a diarylureido-dihalokynurenate compound. Preferred diarylureido-dihalokynurenate compounds are esters (e.g., ethyl esters). Particularly preferred are diphenylureido-dichlorokynurenate compounds.

14 Claims, 11 Drawing Sheets

CARBAMAZEPINE

PHENYTOIN 5,7-DICHLOROKYNURENATE

METHOD FOR TREATING CHRONIC PAIN

CROSS-REFERENCE TO RELATED APPLICATIONS

This application claims the benefit of U.S. Provisional Application for Patent Ser. No. 60/724,540, filed on Oct. 7, 2005, which is incorporated herein by reference.

FIELD OF THE INVENTION

The invention relates to methods for treating chronic pain. More particularly, the invention relates to methods for treating chronic pain by administering to a patient a pain ameliorating amount of a diarylureido-dihalokynurenate compound.

BACKGROUND OF THE INVENTION

Acute pain has been characterized as a normal sensation triggered in the nervous system to alert the individual to possible injury. Chronic (neuropathic) pain, on the other hand, is a persistent discomfort in which pain signals reverberate in the nervous system for prolonged periods of time (e.g., weeks, months, or years). Chronic pain may be initiated by an initial traumatic event, such as a sprained back, a serious infection, neurologic or nerve injury and the like, or there may be an ongoing root cause of pain, such as arthritis, cancer, or inflammation. Some people suffer from chronic pain even in the absence of any past injury or evidence of bodily damage. Common chronic pain conditions include headaches, low back pain, cancer pain, arthritis pain, neurogenic pain (i.e., pain resulting from damage to the peripheral nerves or to the central nervous system itself), and psychogenic pain (pain not due to past disease or injury or any visible sign of damage inside or outside the nervous system).

A variety of treatments have been proposed and evaluated for the treatment of chronic pain, including medications, acupuncture, local electrical stimulation, brain stimulation, and surgery. Psychotherapy, relaxation therapy, biofeedback, and behavior modification have also been employed in attempts to treat chronic pain. Despite the many proposed therapies, chronic pain remains an important and increasingly common medical complaint, the root causes of which are often difficult to determine, and which frequently are difficult to treat and control.

Studies on the cellular and molecular mechanisms of chronic pain syndromes have focused attention on maladapted activity of voltage sensitive sodium channels in chronic pain syndromes, e.g., over activity of signal conduction mediated by the voltage sensitive sodium channels in the pain sensitive neurons. The other major biologic system implicated in origination of chronic pain is the N-methyl-D-aspartate (NMDA) receptors e.g., overactive signal transduction mediated by the NMDA subtype of glutamatergic receptors in the CNS is an important manifestation of chronic pain.

There is an ongoing need for methods of treating chronic neuropathic pain. The present invention provides methods for treating chronic pain utilizing diarylureido-dihalokynurenate compounds that reduce the activity of sodium channels in a use-dependent manner and target the NMDA receptor through its glycine binding site.

SUMMARY OF THE INVENTION

The present invention provides a method for the treatment of chronic pain in a mammal. The method comprises administering a pain relieving amount of a diarylureido-dihalokynurenate compound to a mammal (e.g., a human) suffering from chronic pain. For oral administration, the diarylureido-dihalokynurenate compounds are preferably esters, more preferably esters of alcohols having one to three carbon atoms (e.g., methyl, ethyl, propyl). The diarylureido-dihalokynurenate compounds have an affinity for binding to both the strychnine-insensitive glycine binding site on the N-methyl-D-aspartate (NMDA) receptor and for binding to voltage dependent sodium ion channels.

In some preferred embodiments the diarylureido-dihalokynurenate compounds are diphenylureido-dichlorokynurenic acid (DCUKA) compounds, particularly esters thereof.

Particularly preferred are compounds having the formula (I),

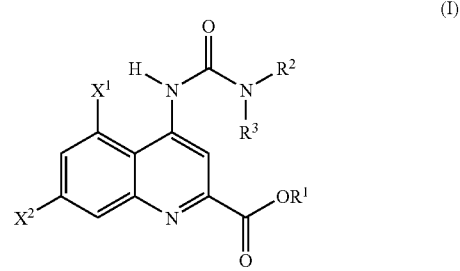

wherein $R^1$ represents hydrogen or an alkyl group of 1 to 12 carbon atoms or a cycloalkyl of 3 to 8 carbon atoms; $R^2$ and $R^3$ each independently represent phenyl or phenyl having one or more alkoxy substituent; and $X^1$ and $X^2$ each independently represent a halogen (e.g., chlorine, bromine, iodine).

In cell death studies utilizing cerebellar granule cells grown in culture adapted for measuring glutamate-induced cell death, diarylureido-dihalokynurenate compounds significantly reduced or eliminated cell death. In these studies, using 100 micromolar glutamate to induce cell death, a 10 micromolar dose of a diphenylureido-dichlorokynurenic acid reduced cell death by more than 50 percent, compared to controls with no treatment. A 100 micromolar dose of diarylureido-dihalokynurenic acid completely protected the cells from glutamate-induced cell damage.

DETAILED DESCRIPTION OF PREFERRED EMBODIMENTS

Figure 1:
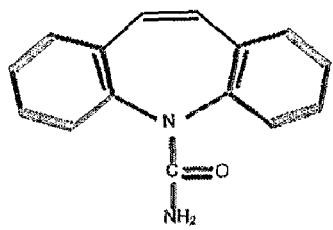
FIG. 1 illustrates the pharmacophores present in (carbamazepine, phenytoin, and dichlorokynurenic acid, which was discovered and utilized to design an effective agent that binds to both the NMDA receptor and sodium ion channels (e.g. diphenylureido-dichlorokynurenic acid compounds such as DKUKA, DCUK-OMe and DCUK-OEt).
Figure 1:
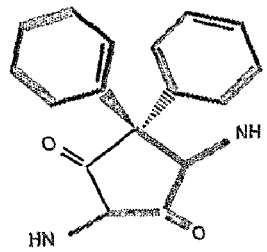
Figure 1:
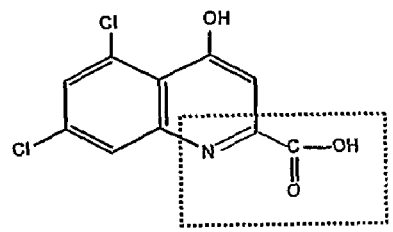
Figure 1:
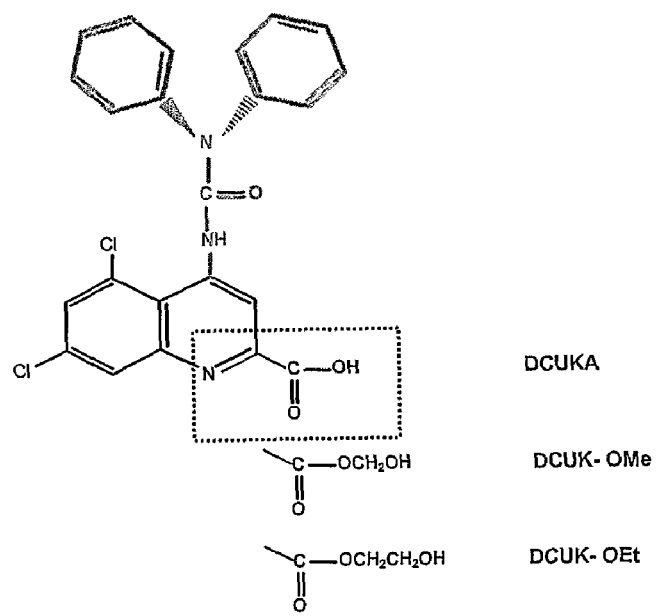

A method for treating chronic pain in a mammal comprises administering a pain relieving amount of a diarylureido-dihalokynurenate compound to a mammal (e.g., a human) suffering from chronic pain. Suitable illustrative compounds are described in U.S. Pat. No. 6,962,930 to Tabakoff, et al., incorporated herein by reference. In some preferred embodiments, the diarylureido-dihalokynurenate compounds are esters, preferably esters of alcohols having one to twelve carbon atoms. Particularly preferred compounds are ethyl esters.

In other preferred embodiments the diarylureido-dihalokynurenate compounds are diphenylureido-dichlorokynurenic acid (DCUKA) compounds. More preferably the DCUKA compounds are esters, particularly esters of alcohols having one to three carbon atoms.

To prepare the corresponding esters, DCUKA can be esterified with appropriate alcohols such as the monohydric alcohols containing 1 to 12 carbon atoms; the monosaccharides such as the pyranoses, e.g., a-D-glucopyranose, β-D-glucopyranose, and the like; natural hydroxy amino acids such as serine, threonine, tyrosine; synthetic hydroxy amino acids such as statine, isostatine, benzylstatine, cyclohexylstatine, α-amino-β-hydroxyvaleric acid, γ-amino-β-hydroxyvaleric acid, hydroxylysine, 3-hydroxyproline, 4-hydroxyproline, and the like.

Particularly preferred diarylureido-dihalokynurenate compounds have the formula (I):

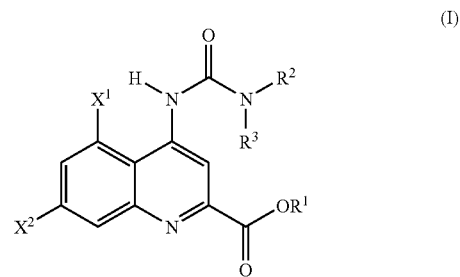

a tautomer thereof, or a pharmaceutically acceptable acid addition salt thereof;

wherein $R^1$ represents hydrogen or an alkyl group of 1 to 12 carbon atoms, preferably 1 to 3 carbon atoms, or a cycloalkyl of 3 to 8 carbon atoms; $R^2$ and $R^3$ each independently represent phenyl or phenyl having one or more alkoxy substituent (e.g., methoxy, ethoxy, propoxy, isopropoxy); and $X^1$ and $X^2$ each independently represent a halogen substituent (e.g., chlorine, bromine, iodine). The substituents $X^1$ and $X^2$ can be the same or different. Similarly, the substituents $R^2$ and $R^3$ can be the same or different. Preferably, $R^1$ is an alkyl group of 1 to 3 carbon atoms, more preferably an ethyl group. Preferably, $X^1$ and $X^2$ are each a chlorine substituent.

Certain preferred diarylureido-dihalokynurenate compounds include a N,N-diphenyl-4-ureido-5,7-dichloro-2-carboxyquinoline ester, a tautomer thereof, and an acid addition salt thereof. Particularly preferred diarylureido-dihalokynurenate compounds are N,N-diphenyl-4-ureido-5,7-dichloro-2-carboxyquinoline (DCUKA), N,N-diphenyl-4-ureido-5,7-dichloro-2-carboxy quinoline methyl ester (DCUK-OMe), N,N-diphenyl-4-ureido-5,7-dichloro-2-carboxy quinoline ethyl ester (DCUK-OEt), and a pharmaceutically acceptable acid addition salt thereof.

The acid addition salts of the foregoing compounds preferably are non-toxic, pharmaceutically acceptable salts suitable for medical use. Other salts may, however, be useful in the preparation of the compounds according to the invention or in the preparation of their non-toxic pharmaceutically acceptable salts. Suitable pharmaceutically acceptable salts of the compounds of this invention include alkali metals salts, e.g., sodium or potassium salts; alkaline earth metal salts, e.g., calcium or magnesium salts; and salts formed with suitable organic ligands e.g., quaternary ammonium salts. When appropriate, acid addition salts may, for example, be formed by mixing a solution of the compound prepared according to the invention with a solution of a pharmaceutically acceptable non-toxic acid such as hydrochloric acid, fumaric acid, maleic acid, succinic acid, acetic acid, citric acid, tartaric acid, carbonic acid, or phosphoric acid.

Preferably, the diarylureido-dihalokynurenate compounds are administered to the mammal in an amount in the range of about 1 to about 10 milligrams per kilogram of body weight.

The diarylureido-dihalokynurenate compounds have an affinity for binding to both the strychnine-insensitive glycine binding site on the N-methyl-D-aspartate (NMDA) receptor and for binding to voltage dependent sodium ion channels. FIG. 1 illustrates pharmacophores contained in carbamazepine, phenytoin, and dichlorokynurenic acid, which were discovered and utilized to design an effective agent that binds to both the NMDA receptor and sodium ion channels (e.g. the diphenylureido-dichlorokynurenic acid compounds DKUKA, DCUK-OMe and DCUK-OEt). These compounds were designed to incorporate features from both NMDA receptor and sodium channel binding compounds. A synthetic scheme for the preparation of diarylureido-dihalokynurenate compounds, such as DCUKA, is provided in U.S. Pat. No. 6,962,930 to Tabakoff, et al., which is incorporated herein by reference.

Synthesis of DCUKA Ethyl Ester

Reaction 1: (Z)-Diethyl-3,5-dichloroanilinofumarate, Compound 3

A solution of freshly distilled diethyl acetylenedicarboxylate (Compound 1, 1.12 mole, 189.24 g) in tetrahydrofuran (THF; 70 mL) was added (dropwise) to solution of 3,5-dichloroaniline (Compound 2, 1.24 mole, 201.41 g) in THF (122 mL) in a 2 L three-neck flask equipped with a condenser. The solution was refluxed for about 4 hours and then cooled to ambient room temperature. The resulting mixture was concentrated on a rotary evaporator to afford crude (Z)-diethyl-3,5-dichloroanilinofumarate (Compound 3). The cis-isomer (i.e., Z isomer) of Compound 3 was produced at about 82% relative to the trans-isomer. The concentrated reaction mixture containing crude Compound 3 was used, as is, in the following reaction.

Reaction 2: Ethyl 5,7-dichloro-1,4-dihydro-4-oxo-quinoline-2-carboxylate, Compound 4

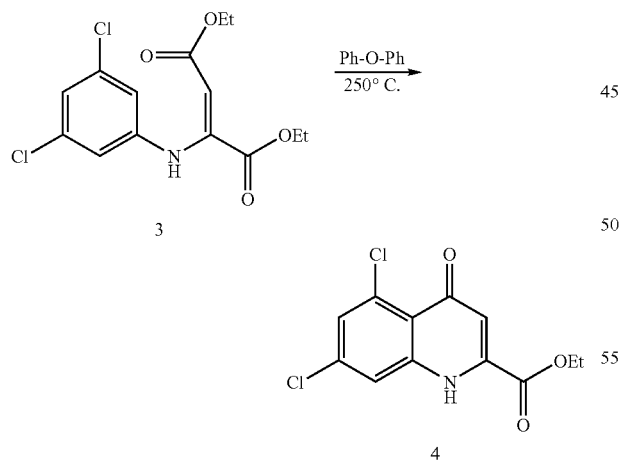

A 5-L three-neck flask equipped with a thermocouple, an addition funnel, and a distillation apparatus was charged with diphenyl ether (about 2.8 L), which was heated to about 244° C. The concentrated reaction mixture containing Compound 3 (about 1.1 mole) from Reaction 1, above, was added from the dropping funnel into the hot diphenyl ether over about 10 minutes with a nitrogen purge. The funnel was rinsed with about 200 mL of diphenyl ether, which was also added to the flask. The resulting mixture was heated at about 244° C. for about 1 hour to cyclize Compound 3 to form Compound 4. The reaction mixture then was cooled to room temperature, at which point Compound 4 crystallized out. The crystallized product was isolated and slurried with ethyl acetate (EtOAc; about 1 L). The crystals were collected and rinsed with EtOAc (3×500 mL), and then dried under high vacuum at room temperature to afford about 269.95 g of Compound 4 (85.8% yield over two steps).

Reaction 3: Ethyl 4-amino-5,7-dichloro-quinoline-2-carboxylate, Compound 5

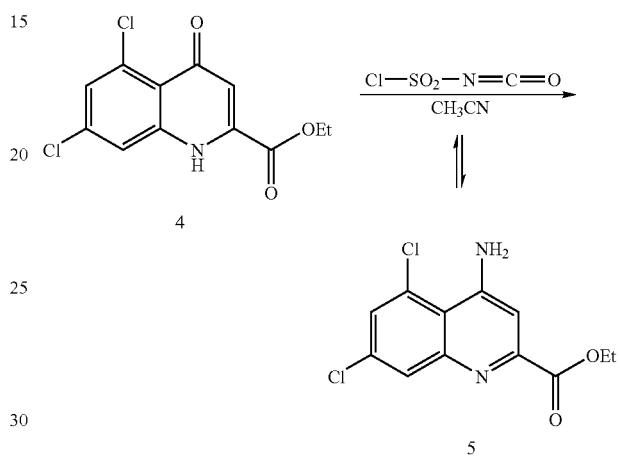

A 12-L three-neck flask equipped with a mechanical mixer, a condenser, and thermocouple was charged with Compound 4 (0.94 mole, 269.1 g) in acetonitrile (ACN; about 4 L), after which chlorosulfonyl isocyanate (0.99 mole, 86 mL) was added (dropwise) via the dropping funnel. Upon completion of the addition, the resulting reaction mixture was refluxed for about 28 minutes. The pH of the mixture was about 0 at this point. The mixture then was cooled slightly, while adding saturated HCl in methanol (MeOH; 500 mL). Subsequently, the mixture was refluxed for about 1 hour, and then allowed to cool to room temperature overnight, during which time crystals formed. The crystals were collected on a sintered glass frit and rinsed with acetonitrile (400 mL and 500 mL). The filter cake was then transferred to a 12 L reactor with a mechanical stirrer. Deionized (DI) water (900 mL) and saturated $Na_2CO_3$ (500 mL) were added to afford mixture having a pH of about 10. Next, the solids in the mixture were collected and slurry rinsed with DI water (3×500 mL). The rinsed product was dried via lyophilization to afford about 268.79 g (63.3% yield) of Compound 5.

Reaction 4: Ethyl 5,7-dichloro-4-([(diphenylamino)carbonyl]amino)quinoline-2-carboxylate, Compound 6

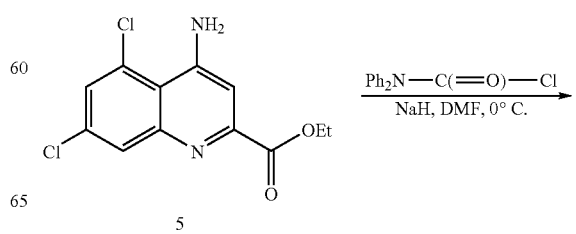

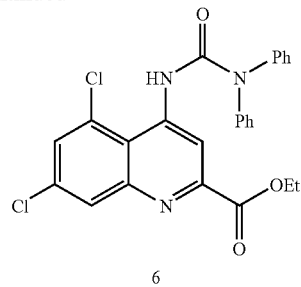

5-L three-neck flask was charged with a cold (<10° C.) solution of Compound 5 (about 0.59 mole, 168.95 g) in N,N-dimethylformamide (DMF) (about 2 L). Diphenylcarbamoyl chloride (0.73 mole, 168.92 g) then was added to the solution. The resulting mixture was maintained below 10° C., sodium hydride (NaH; 1.19 mole, 28.45 g) was added, in portions, over about 1.3 hours, and the reaction mixture was allowed to warm to ambient temperature overnight. Thin layer chromatography (TLC) indicated that some unreacted Compound 5 remained. The reaction mixture was recooled to about 10° C., and additional NaH (about 0.3 mole, 7.11 g) was added. The subsequent reaction was quenched with saturated aqueous ammonium chloride ($NH_4Cl$; about 1.3 L) followed by the addition of 10% aqueous acetic acid (AcOH; 1 L), 20% AcOH (0.5 L), and EtOAc (4 L) to obtain a mixture having a pH of about 4 to 5. The solids present in the flask then were filtered, rinsed with EtOAc (500 mL) and DI water (500 mL), and dried by lyophilization to afford about 229 g of crude Compound 6 and a crude filtrate containing additional Compound 6. The crude Compound 6 was dissolved in dichloromethane ($CH_2Cl_2$; 3 L), back extracted with deionized (DI) water (500 mL) and brine (500 mL). The organic phase was dried over $Na_2SO_4$ (323.30 g) and filtered to afford a solution containing the bulk of the crude Compound 6.

In order to recover additional Compound 6, the crude filtrate described above was separated, the organic phase was back extracted with DI Water, washed with brine (500 mL), and dried over anhydrous sodium sulfate ($Na_2SO_4$; 164.35 g). The resulting dried filtrate was then evaporated to a DMF residue and cooled to about 4° C. overnight to crystallize additional product. The resulting solids were washed with EtOAc (300 mL, <-30° C.), and dried under high vacuum to afford about 39.91 g of additional crude Compound 6.

The additional crude Compound 6 was dissolved in $CH_2Cl_2$ (about 0.25 L) and added to a 2-L sintered glass fritted Büchner funnel containing flash silica gel (680.68 g). The solution containing the bulk of the crude Compound 6 was also added to the Buüchner funnel. The flash silica gel was eluted with $CH_2Cl_2$ (about 13 L) and 2.5% EtOAc/$CH_2Cl_2$ (about 2 L). The combined effluent was evaporated to afford 244.57 g of product, which was dissolved in ethanol (EtOH; 2 L) and $CH_2Cl_2$ (1 L) at reflux. The $CH_2Cl_2$ was then removed by distillation until crystallization occurred. The mixture was cooled in an ice bath for about 1.75 hours, and the crystals were collected and rinsed with EtOH (100 mL and 150 mL, <-20° C.). The crystals were dried at 40° C. for 17 hours to afford about 227.70 g of Compound 6 (DCUK ethyl ester; 80.0% yield). The purity of the product was determined by NMR and high performance liquid chromatography (HPLC) to be about 99.74%. Mass spectral (MS) analysis yielded m/z 480.48 [M+H]+. The water content was determined by Karl Fischer analysis to be about 0.0%.

Reaction 5: 5,7-Dichloro-4-([(diphenylamino)carbonyl]amino)-2-quinolinecarboxylic acid (DCUK Acid); Compound 7

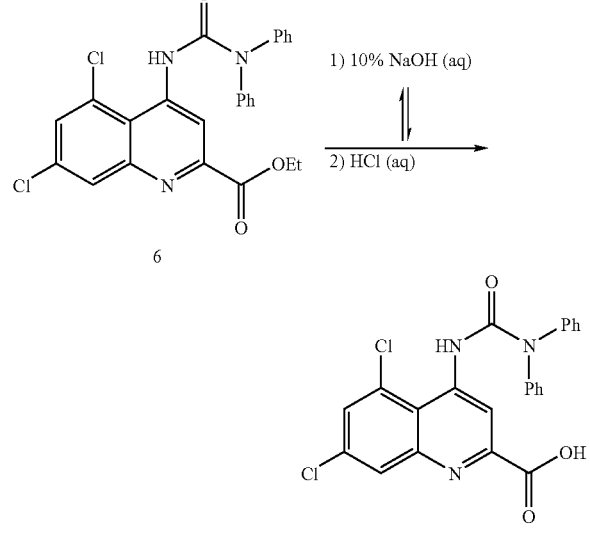

A 500 mL flask was charged with Compound 6 (0.0083 mole, 4.01 g) and 10% NaOH (125 mL). The mixture was refluxed with stirring for about 20 hours, filtered, and then rinsed with DI water (2×50 mL). The resulting bright yellow solids were then dissolved in 2N HCl (60 mL) and $CH_2Cl_2$ (100 mL) was added, with stirring. After stirring for about 15 minutes, crystals were collected, rinsed with DI water (2×50 mL), and dried under vacuum for about 64 hours at room temperature (with the first 2 hours of drying at about 40° C.). About 3.23 g (53.6% yield) of bright yellow crystals of Compound 7 were obtained. The purity of the obtained Compound 7 was about 99.38% (HPLC), with a water content of about 0.04% (Karl Fischer). MS m/z 452.57 [M+H]+. Other batches prepared in substantially the same manner had HPLC purities of about 90-99%, and water contents of about 1 to 1.4%.

In Vitro Testing of DCUKA Activity at NMDA Receptors and Voltage Sensitive Sodium Channels Ligand binding studies and electrophysiological experiments were used to ascertain the characteristics of DCUKA activity in in vitro assays. The activity of DCUKA compounds was compared, in all studies, to compounds which individually contained one or the other pharmacophore which were utilized in the design of the DCUKA compounds (e.g., carbamazepine (CBZ) and dichlorokynurenic acid).

Figure 2:
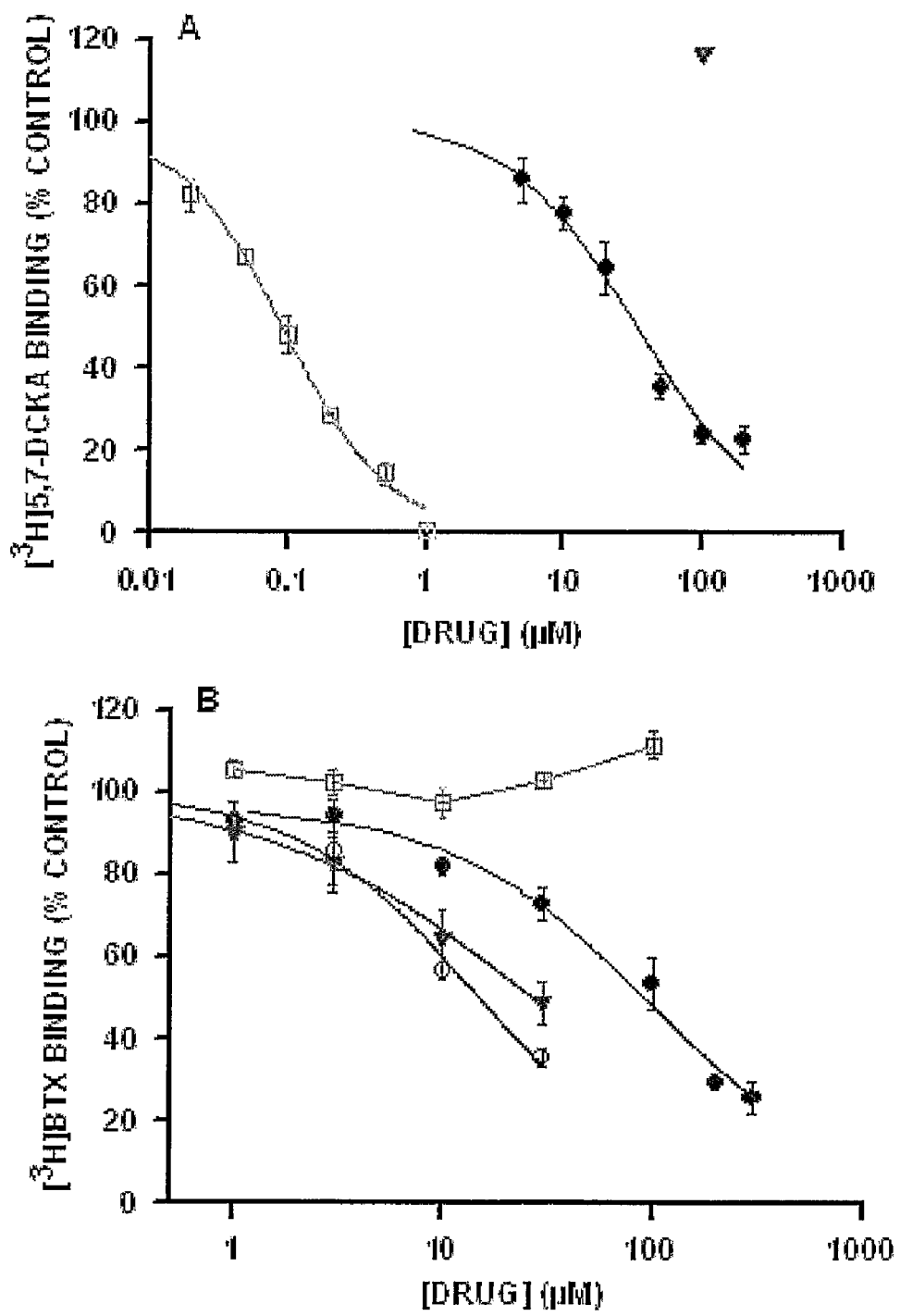
FIG. 2 graphically illustrates effects of the DCUKA compounds on the binding of [$^3$H]5,7-DCKA to rat cortical membranes in Panel A; and the binding of [$^3$H]BTX to rat cortical synaptosomes in Panel B. □5,7-DCKA; ● DCUKA; ▼ DCUK-OMe; ○ DCUKA (depolarized); the graph in Panel A includes a single data point for DCUK-OMe.

FIG. 2 illustrates the results of the ligand binding studies. In FIG. 2 the effects of the DCUKA compounds on the binding of [$^3$H]5,7-dichlorokynurenic acid (DCKA) to rat cortical membranes in Panel A. The binding of [$^3$H]BTX to rat cortical synaptosomes is shown in Panel B. (in the graphs, □=5,7-DCKA; ●=DCUKA; and ▼=DCUK-OMe; ○ DCUKA (depolarized).

From these studies, DCUKA affinities for binding sites on the NMDA receptor and the voltage sensitive sodium channel were ascertained (Table 1). DCUKA had binding affinities in the micromolar range for both the NMDA receptor and the voltage sensitive sodium channel, while the parent structures (i.e., carbamazepine, and dichlorokynurenic acid) bound only to the voltage sensitive sodium channel binding site or to the glycine binding site on the NMDA receptor, respectively. In addition, the methyl ester of DCUK also bound to the voltage sensitive sodium channel binding site with greater affinity than the parent compound DCUKA.

TABLE 1

| Compound | $IC_{50}$ (μM) [$^3$H]5,7-DCKA binding | $IC_{50}$ (μM) [$^3$H]BTX binding |
| --- | --- | --- |
| DCUKA | 28 | 76 (30) |
| DCUK-OMe | none | 25 |
| CBZ | none | 71 (56) |
| 5,7-DCKA | 0.11 | none |

$IC_{50}$ values for [$^3$H]batrachotoxinin (BTX) binding obtained under depolarizing conditions (135 mM KCl) are given in parentheses. In Table 1, the percentage of displacement obtained in the presence of 200 μM DCUKA is given in parentheses.
CBZ = carbamazepine;
none = no displacement at 100 μM Electrophysiological analysis of the characteristics of DCUKA activity revealed that these compounds have fully reversible binding and inhibitory activity at NMDA receptors composed of NR1 and NR2B subunits. On the other hand, glycine was only partially able to reverse the inhibitory activity of DCUKA compounds on NMDA receptors composed of NR1 and NR2A subunits. This phenomenon is illustrated in FIG. 3.

Figure 3:
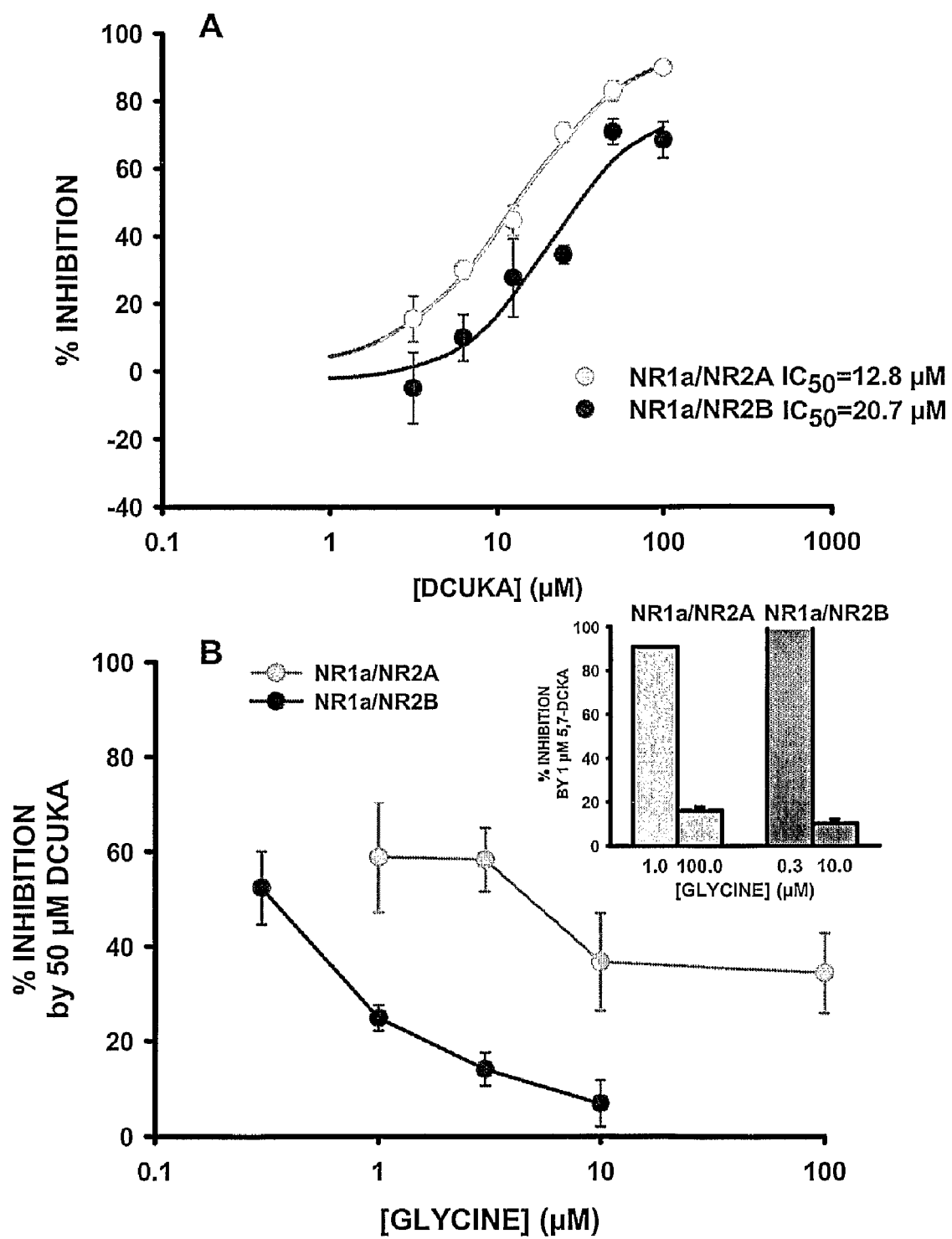
FIG. 3 graphically illustrates the electrophysiologic properties of DCUKA at the NMDA receptor. Panel A: Concentration-inhibition curves comparing the potencies of DCUKA to inhibit NMDA-evoked currents. Panel B: inhibition of NMDA-evoked currents by 25 µM DCUKA in the presence of increasing concentrations of glycine. Inset, effects of 1 µM 5,7-DCKA on NMDA-evoked currents in the presence of $EC_{50}$ concentrations and maximal concentrations of glycine in oocytes expressing NR1a/NR2A or NR1a/NR2B receptors; the graph in Panel A includes a single data point for DCUK-OMe.

In FIG. 3, Panel A shows concentration-inhibition curves comparing the potencies of DCUKA to inhibit NMDA-evoked currents (100 μM) in the presence of $EC_{50}$ concentrations of glycine (6 or 0.4 μM) to evoke maximal responses in oocytes expressing NR1a/NR2A or NR1a/NR2B receptors, respectively. Panel B demonstrates inhibition of NMDA-evoked currents by 25 μM DCUKA in the presence of increasing concentrations of glycine. The inset shows effects of 1 μM 5,7-DCKA on NMDA-evoked currents in the presence of $EC_{50}$ concentrations and maximal concentrations of glycine in oocytes expressing NR1a/NR2A or NR1a/NR2B receptors.

Figure 4:
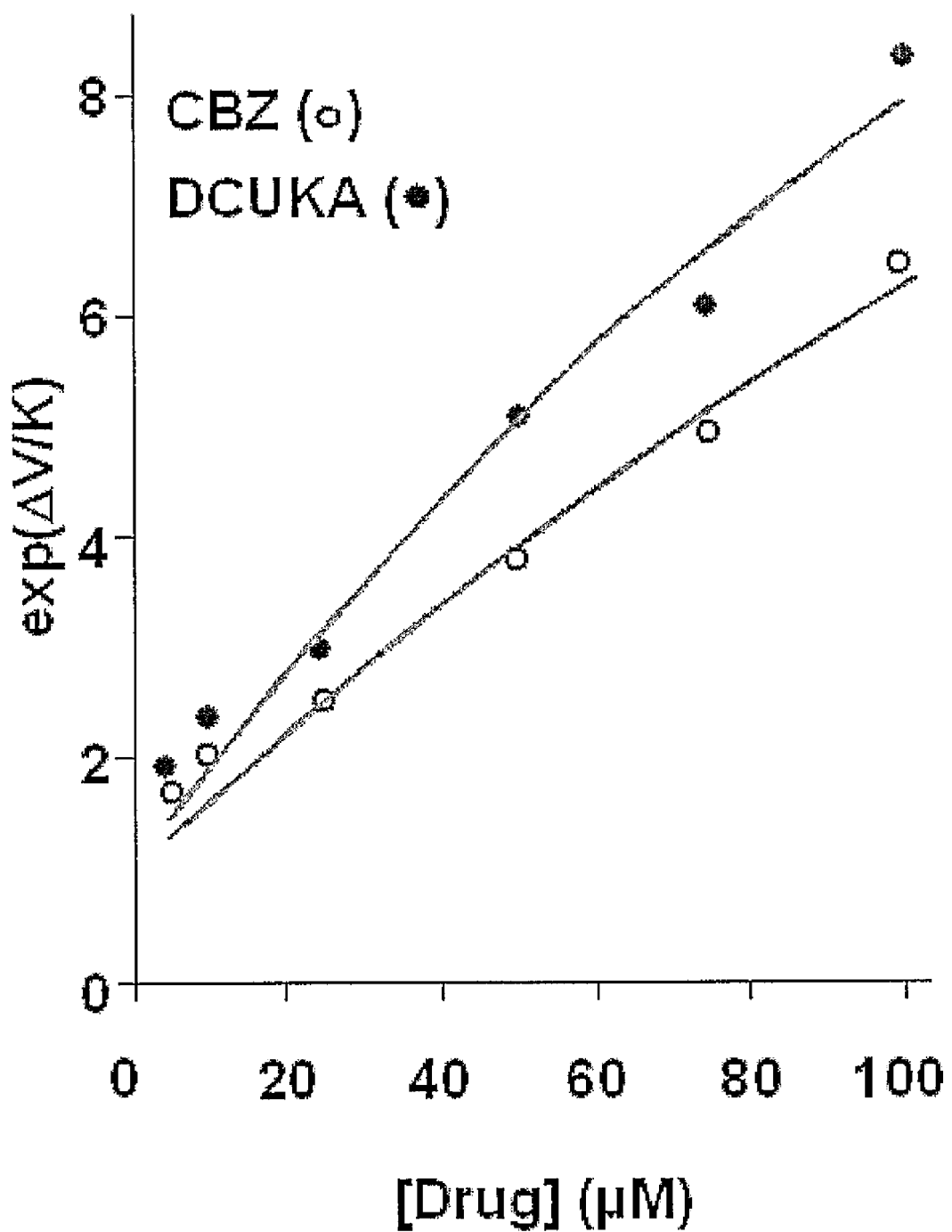
FIG. 4 graphically compares drug affinities of DCUKA and carbamazepine (CBZ) for resting and inactivated states of expressed voltage sensitive sodium channels.
Figure 5:
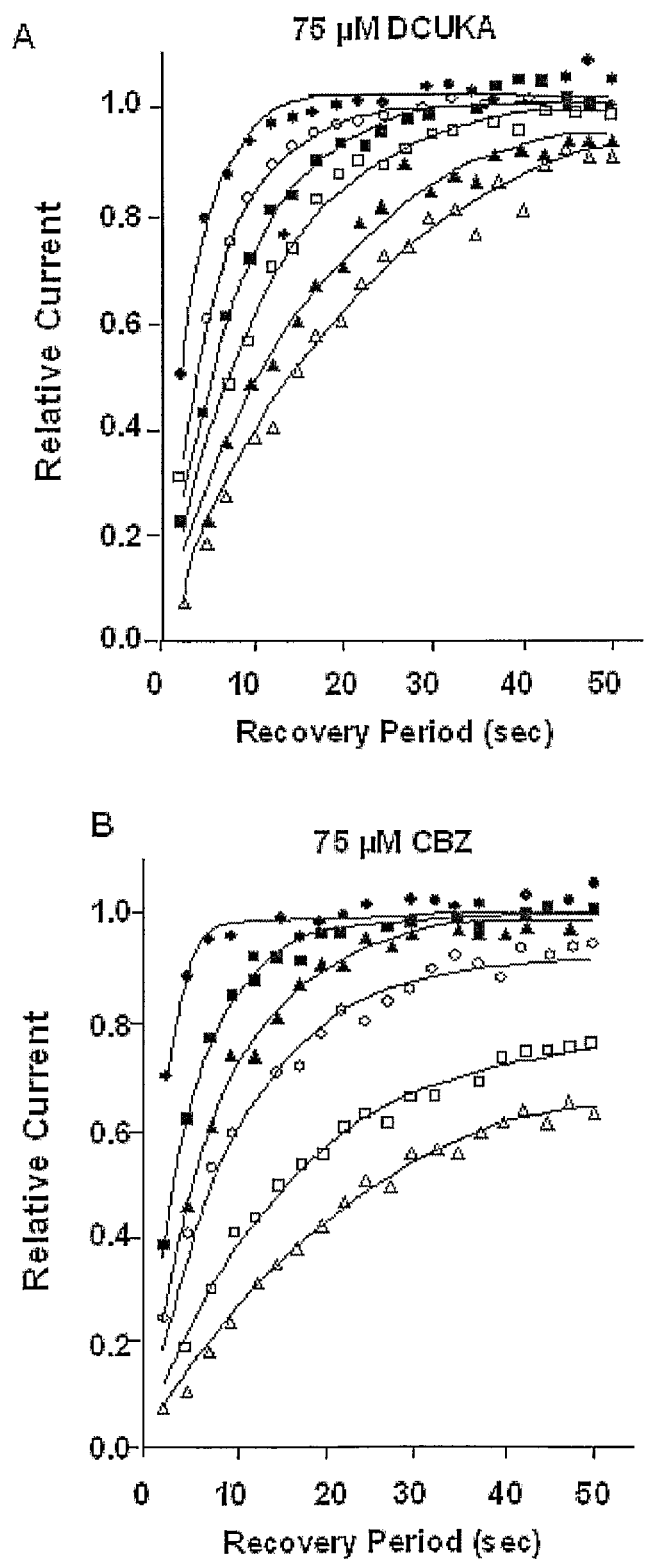
FIG. 5 graphically illustrates effects of DCUKA and CBZ on the recovery from inactivation at different holding potentials. The data in Panels A and B are from the same cell in the absence (●, −100 mV; ■, −80 mV; ▲, 70 mV) and presence (○, −100 mV; □, −80 mV; Δ, −70 mV) of 75 μM test substance.

With regard to voltage sensitive sodium channels, experiments utilizing the neuronal recombinant sodium channel protein (Nav1.2) demonstrated that DCUKA compounds have significant similarities to the mechanisms of action of carbamazepine. On the other hand, there were also some important differences including the rate of recovery from inactivation and the higher affinity of the DCUKA compounds for the inactivated channels. FIGS. 4 and 5 illustrate some of these phenomena.

In FIG. 4, drug affinities of DCUKA and carbamazepine (CBZ) are compared for resting and inactivated states. The data were fitted by the equation $\exp(\Delta V/k) = [1+(D/K_I)]/[1+(D/K_R)]$, where k is the slope factor of the inactivation curve, D is the concentration of DCUKA or CBZ, and $K_I$ and $K_R$ are the dissociation constants for inactivated states and the resting state. For DCUKA, $K_I$=9.8 μM and $K_R$=244 μM; for CBZ, $K_I$=14.6 μM and $K_R$=400 μM.

In FIG. 5 the effects of DCUKA and CBZ on the recovery from inactivation at different holding potentials are illustrated. The recovery from inactivation was measured with a two-pulse protocol that consisted of a 100-ms conditioning pulse to 0 mV from –100, –80, or –70 mV holding potentials, followed by an interpulse interval of varying duration (2.5-50 ms) at the same holding potential, with a final test pulse to 0 mV for 10 ms. The amplitudes of the currents elicited by the test pulses were normalized with respect to the currents elicited by the conditioning pulses in each series and were plotted as a function of the recovery interval. The data were fit to a rising exponential function according to the equation $\gamma = 1 - A\exp(t/\tau)$, where γ is the normalized current, A the fractional recovery of current at infinite interpulse intervals (expected to be 1), t the interpulse interval, and τ the time constant for recovery. The data in Panels A and B are from the same cell in the absence (●, –100 mV; ■, –80 mV; ▲, 70 mV) and presence (○, –100 mV; □, –80 mV; Δ, –70 mV) of 75 μM of the test substances.

The actions of anticonvulsants on voltage sensitive sodium are significant in light of the recent findings of the inventors that CBZ shows preferential inhibition of type 1.7 sodium channels, found predominantly in sensory and sympathetic neurons. The similarity of action of DCUKA and CBZ on Nav1.2 sodium channels predicts that DCUKA will have similar selectivity on 1.7 sodium channels.

In Vivo Studies of DCUKA Actions in Chronic Pain Models

Figure 6:
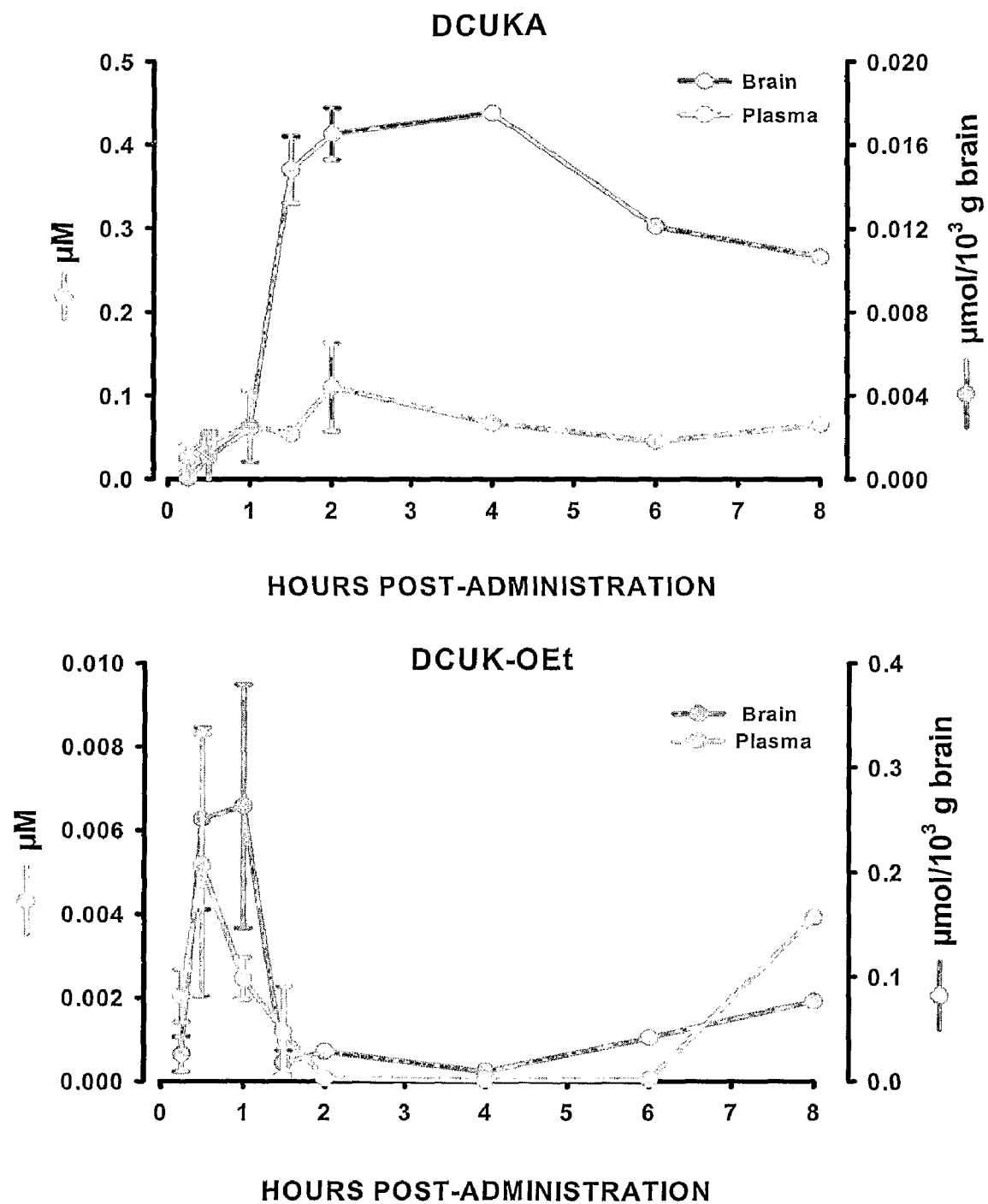
FIG. 6 shows a graph of plasma and brain levels of DCUKA and DCUKA ethyl ester following oral administration of DCUK-OEt to rats.

While the acid forms of the diarylureido-dihalokynurenic acid compounds are detectable in the brain after intravenous or intraperitoneal injection, "prodrug" versions (e.g., esters) were prepared to enhance transport across the blood-brain barrier. FIG. 6 illustrates the brain levels of DCUKA after administration of DCUKA itself, the DCUK-O-methyl ester and the DCUK-O-ethyl ester. Utilization of the ethyl ester of the DCUKA produced a compound that generated significantly improved levels of DCUKA in the brain over a period of at least 2 hours and probably longer following intraperitoneal administration. Accordingly, ethyl esters of the diarylureido-dihalokynurenate compounds are particularly preferred (e.g., DCUK-OEt).

Oral administration has been the major route of drug administration for the treatment of many diseases. FIG. 6 shows a graph of brain levels of DCUKA, and DCUKA generated in situ from DCUKA ethyl ester following oral administration DCUK-OEt to rats. Groups of rats were administered 200 mg/kg DCUK-OEt prepared as an emulsion in gelatin:canola oil (50:50) by oral gavage and sacrificed at 0.25, 0.5 1, 1.5, 2, 4, 6, and 8 hours following administration, in order to collect the blood and brains for analysis. Plasma and brain levels of DCUKA and DCUK-OEt were analyzed by liquid chromatographic separation and mass spectrometric detection. Orally administered DCUK-OEt was converted to DCUKA by plasma and brain carboxylesterases. Peak levels of plasma DCUK-OEt were reached by about 1 hour post-administration, and fell to low levels by about 2 hours. DCUKA plasma levels peaked at about 2 hours and then fell off slowly over the next 4 hours. Brain DCUK-OEt levels peak at about 1 hour post-administration. Brain DCUKA levels peaked at about 2 to 3 hours and exhibited a very slow rate of elimination with DCUKA levels still elevated at about 8 hours post-administration.

Figure 7:
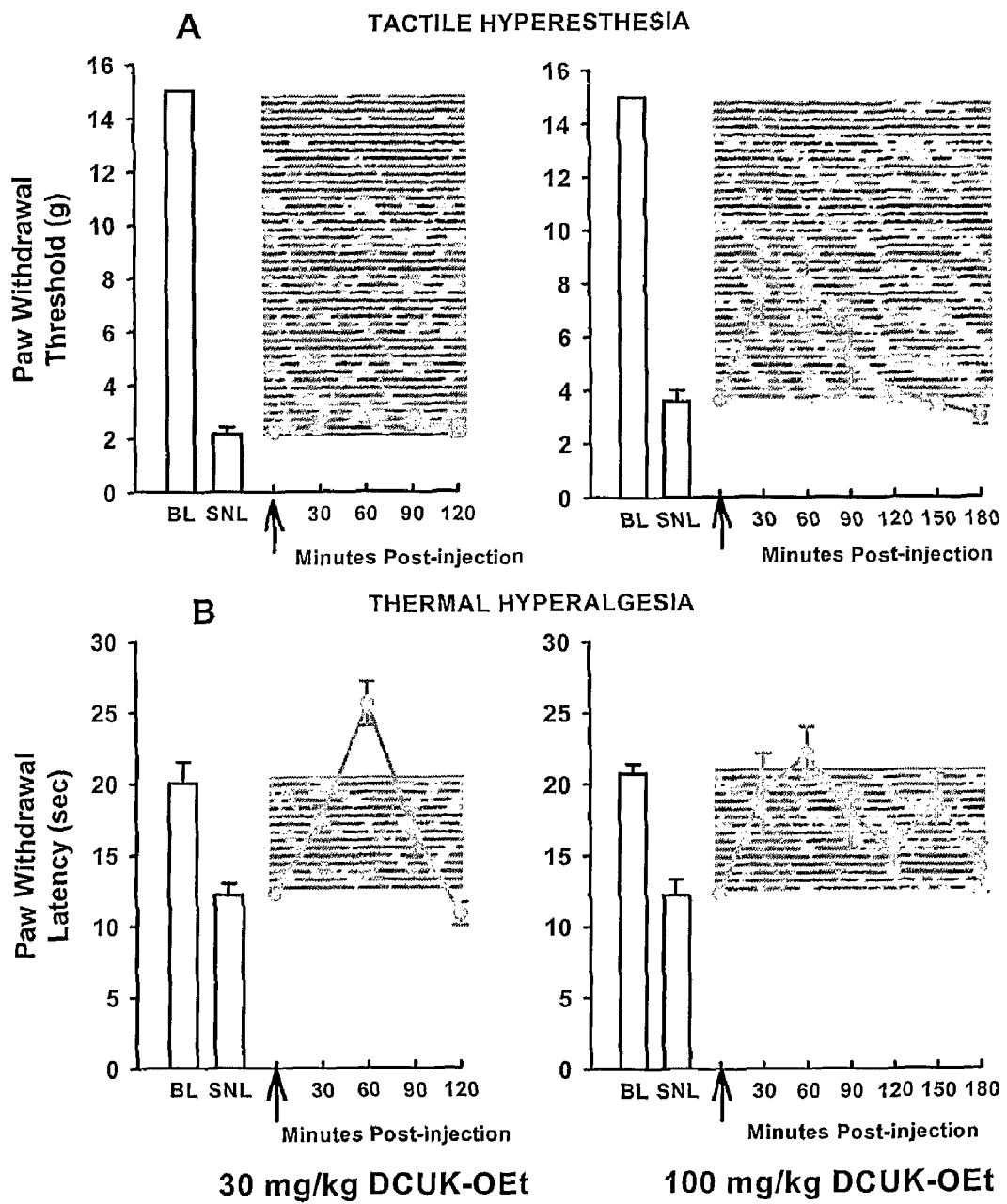
FIG. 7 provides graphs showing attenuation of tactile (Panel A) and thermal (Panel B) hyperalgesia in animals following spinal nerve ligation (SNL).

FIG. 7 illustrates the scheme for testing the DCUK ethyl ester in neuropathic pain models. In FIG. 7 graphs showing attenuation of tactile (Panel A) and thermal (Panel B) hyperalgesia in animals following spinal nerve ligation (SNL) are provided. DCUK-OEt (30 or 100 mg/kg) was administered at the time indicated by the arrow. Hyperalgesic responses were followed for the next 180 minutes. The shaded area represents the area of hyperalgesia produced by SNL. BL on the X-axis represents the baseline response of animals prior to spinal nerve ligation. SNL represents the response of the animals after spinal nerve ligation and prior to receiving the DCUKA ethyl ester. It can be seen that thermal hyperalgesia is normalized by administration of DCUKA ethyl ester to a greater extent than tactile hyperalgesia.

Figure 8:
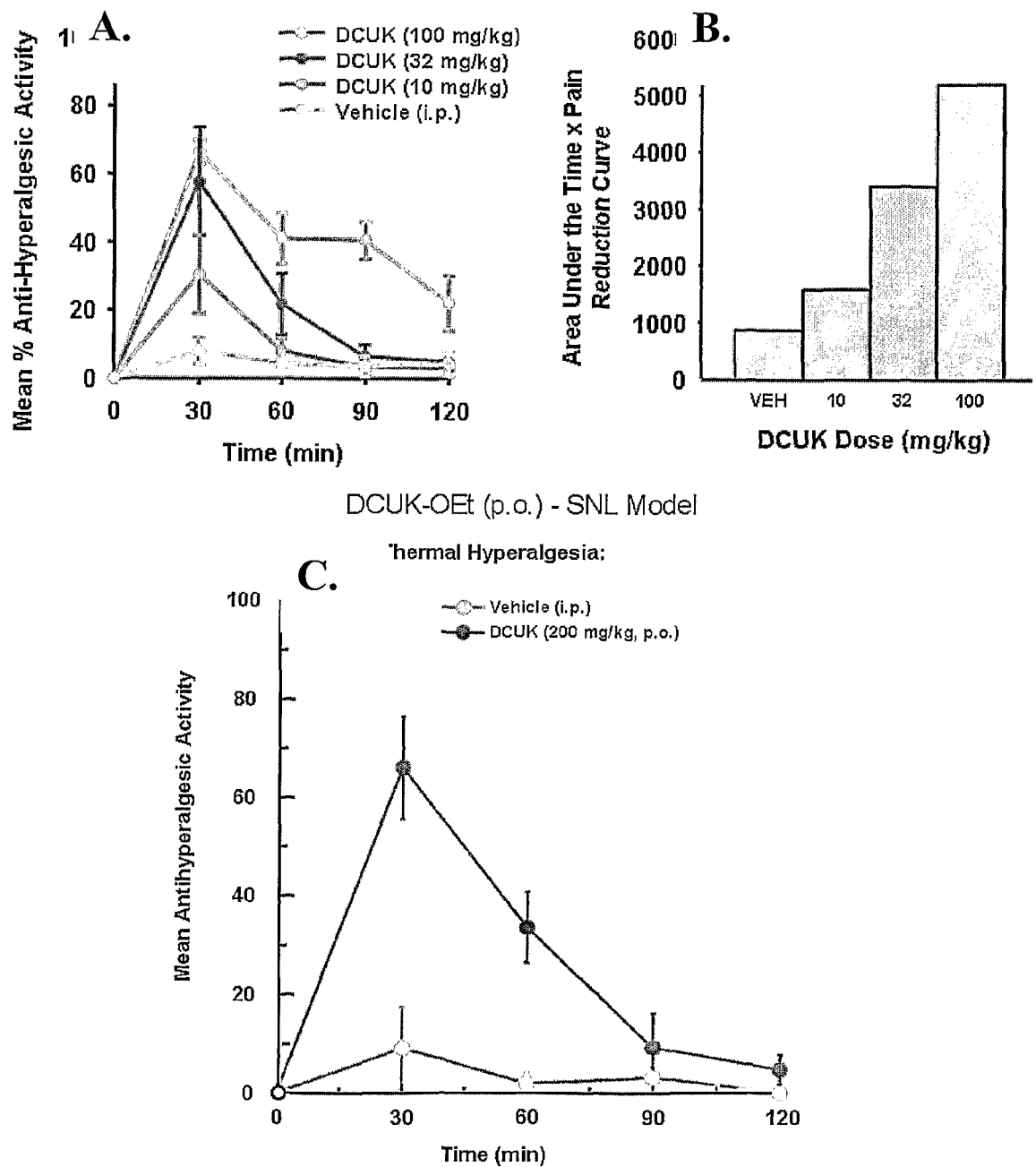
FIG. 8 graphically illustrates the dose-dependent attenuation of thermal hyperalgesia in animals following spinal nerve ligation (SNL). Panel A: Dose-dependent time course of anti-hyperalgesic actions of DCUK-OEt following i.p. administration. Panel B: Overall anti-hyperalgesic actions of DCUK-OEt expressed as the area-under-the-curves shown in panel A. Panel C: Time course of anti-hyperalgesic actions of DCUK-OEt following oral administration.

FIG. 8, Panel A, illustrates the dose-response increased inhibition of thermal hyperalgesia produced by i.p. administration of DCUK-OEt, with 75% inhibition achieved at 100 mg/kg. The overall anti-hyperalgesic effects over the course of the 2 hour testing period are depicted by the area-under-the-curve plot in FIG. 8, Panel B. DCUK-OEt was also found to reduce thermal hyperalgesia by about 70% following oral administration of 200 mg/kg DCUK-OEt emulsion. A 45% inhibition of thermal hyperalgesia was been observed at a dose of about 150 mg/kg DCUK-OEt (p.o.).

Other Activities of DCUKA Compounds

DCUKA ethyl ester was evaluated in other behavioral and physiologic paradigms useful in the treatment of neuropathic pain syndromes. The structure of the DCUKA compounds, and the experiments performed assessing the effects of DCUKA on NMDA receptors, indicated that DCUKA compounds have significant anxiolytic actions. DCUKA ethyl ester was tested in mice utilizing the "elevated-plus" maze for measure of a drug's anxiolytic actions. The results illustrated in FIG. 8 clearly demonstrate the anxiolytic actions of DCUKA ethyl ester in this animal model of anxiety. FIG. 8 presents the results of these studies.

Figure 9:
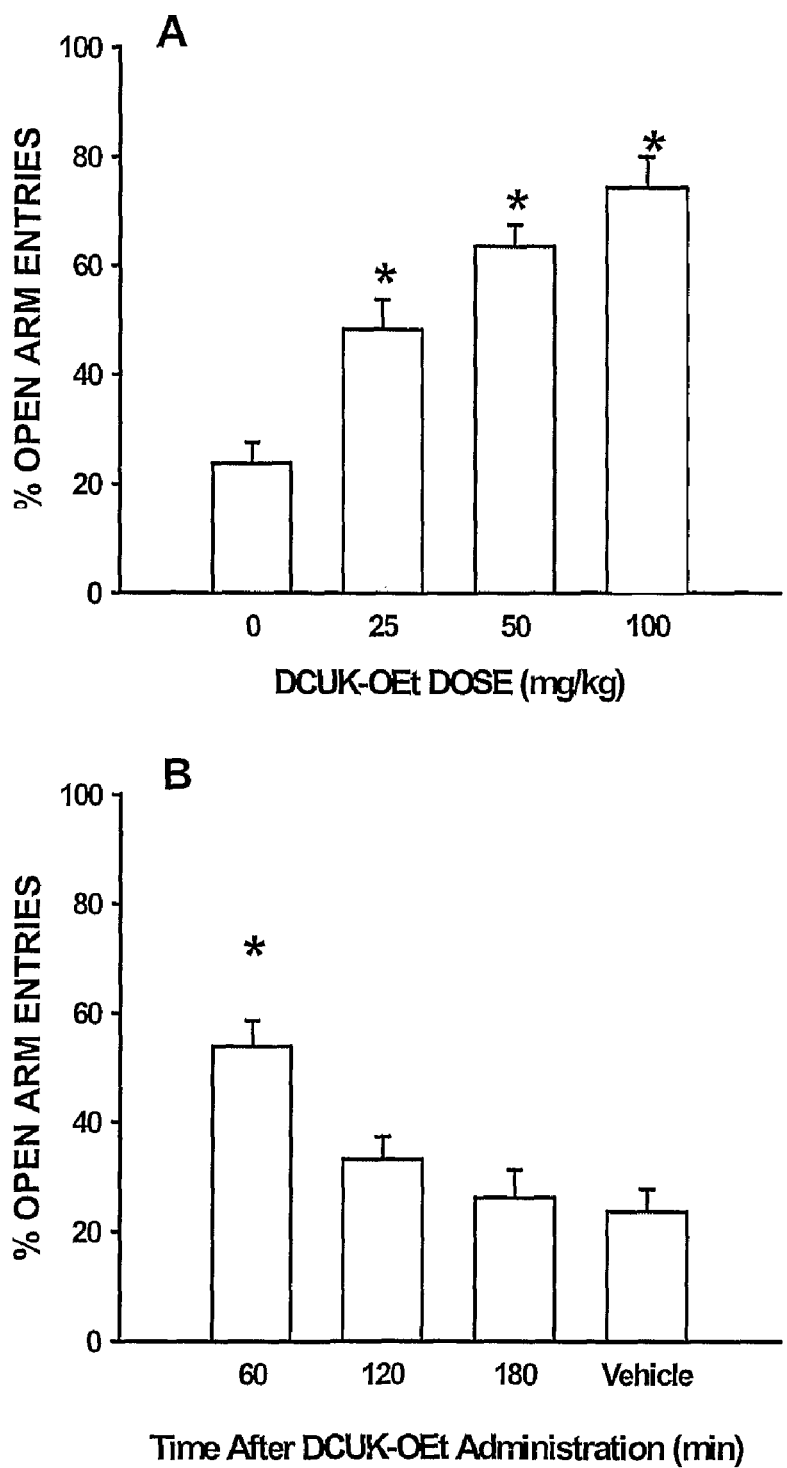
FIG. 9 graphically illustrates anxiolytic effects of DCUK-OEt in C57BL/6 mice. Panel A: Mice were administered (i.p.) the indicated doses of DCUK-OEt 60 minutes before behavioral testing on the elevated-plus maze. The number of and time spent in the open arms of the plus-maze were recorded. Panel B: Groups of mice were administered (i.p.) 50 mg/kg DCUK-OEt and tested at the indicated times. In both panels, vehicle-treated mice were tested 60 minutes after injection of vehicle. The asterisk (*) over the graph bars indicates P<0.05 compared to vehicle control group.

In FIG. 9 anxiolytic effects of DCUK-OEt in C57BL/6 mice are demonstrated. In Panel A, mice were administered (i.p.) the indicated doses of DCUK-OEt about 60 minutes before behavioral testing on the elevated-plus maze. The number of times entered and the time spent in the open arms of the plus-maze were recorded. In Panel B, groups of mice were administered (i.p.) 50 mg/kg DCUK-OEt in an injection vehicle (5% TWEEN 80/0.5% methylcellulose) and tested at the indicated times with comparison to mice injected with vehicle alone. In both panels, mice treated with vehicle alone (i.e., absent the DCUKA compound) were tested 60 minutes after injection of vehicle. A greater percent of time spent in the open arms indicates an anxiolytic action of the drug. Significant differences in the percent time spent on the open arms of the maze are evident at doses as low as 25 mg/kg. Similar results were obtained if we plotted entries into the open arms of the maze rather than the time spent in the open arms.

Additional Beneficial Actions of DCUKA

A manifestation of the over activity of NMDA receptors is the accompanying cell damage and cell death that occurs from the overloading of the cell with calcium and sodium. Studies utilizing cerebellar granule cells grown in culture adapted for measuring glutamate (i.e., glutamate-rich culture medium) induced cell death demonstrated the ability of DCUKA to prevent cell death. In these studies utilizing 100 micromolar glutamate, 10 micromolar DCUKA was able reduce cell death by more than 50 percent. Surprisingly, 100 µM DCUKA completely protected the cells from glutamate-induced damages. FIG. 9 illustrates the results of these studies.

Figure 10:
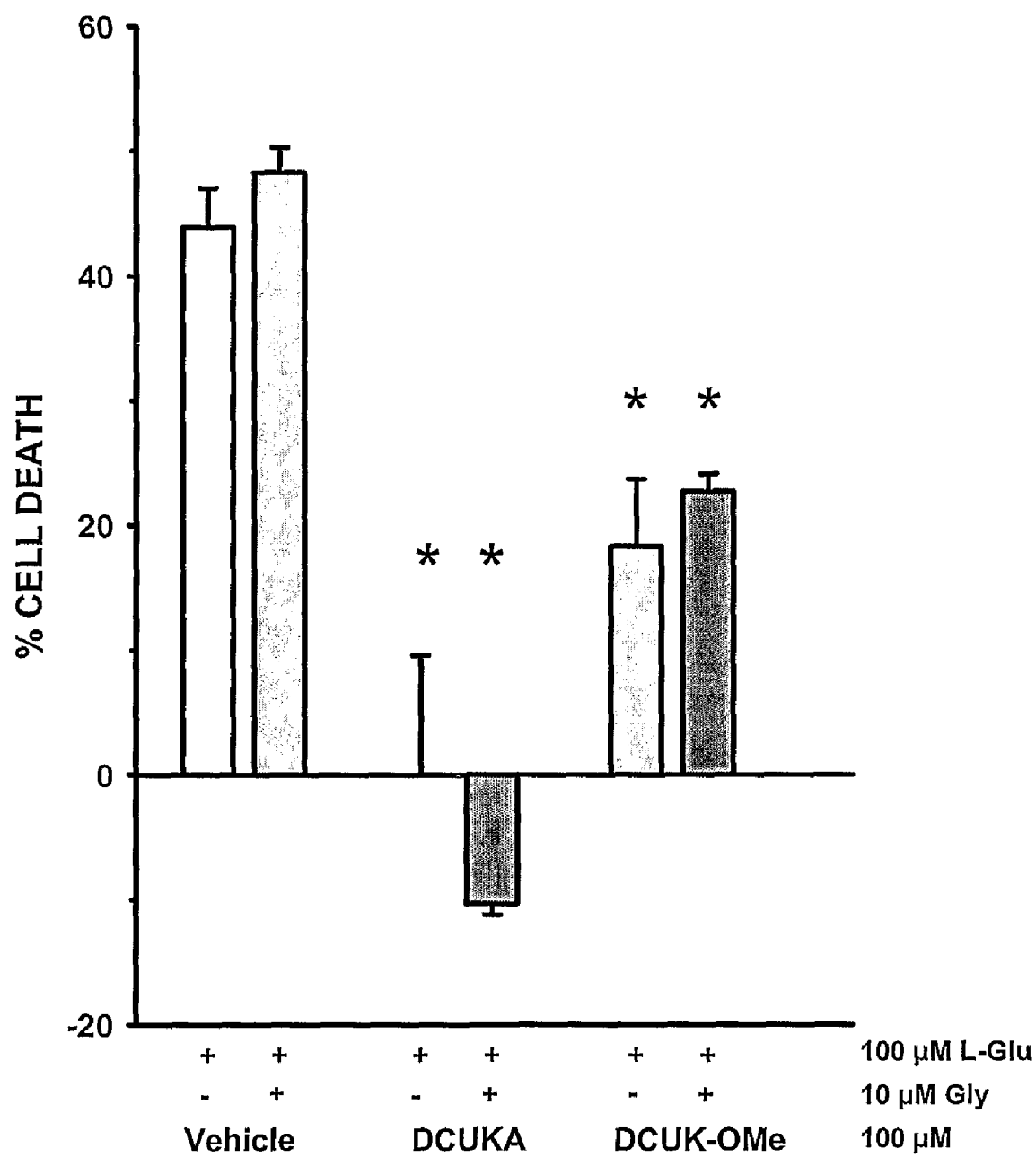
FIG. 10 shows effects of DCUKA and DCUK-OMe on glutamate-induced excitotoxic cell death in primary cultures of rat cerebellar granule cells. The data are expressed as a percentage of cell death relative to the control cultures. The results obtained are recorded as means±S.E. in which *P<0.05 from the corresponding no-drug condition (two-way ANOVA with post-hoc Dunnett's tests).

FIG. 10 shows effects of DCUKA and DCUK-OMe on glutamate-induced excitotoxic cell death in primary cultures of rat cerebellar granule cells. The data are expressed as the percentage of cell death relative to the control cultures. The results obtained are recorded as means±S.E. in which *$P<0.05$ from the corresponding no-drug condition (two-way ANOVA with post-hoc Dunnett's tests).

Other Attractive Physiological and Behavioral Actions of DCUKA

DCUKA compounds have substantial anticonvulsant properties. Given the structure of DCUKA, and some of biochemical/electrophysiological findings, DCUKA compounds can be of value in ameliorating partial, petit mal seizures as well as grand-mal epilepsy and have neuroprotective actions in epileptic syndromes. Preliminary data showing such effects was obtained through the NINDS antiepileptic compound testing program. DCUK-methyl ester was also tested in a mouse model of petit mal epilepsy. The results shown in FIG. 11 illustrate that DCUK may also have efficacy in controlling petit mal epilepsy.

Figure 11:
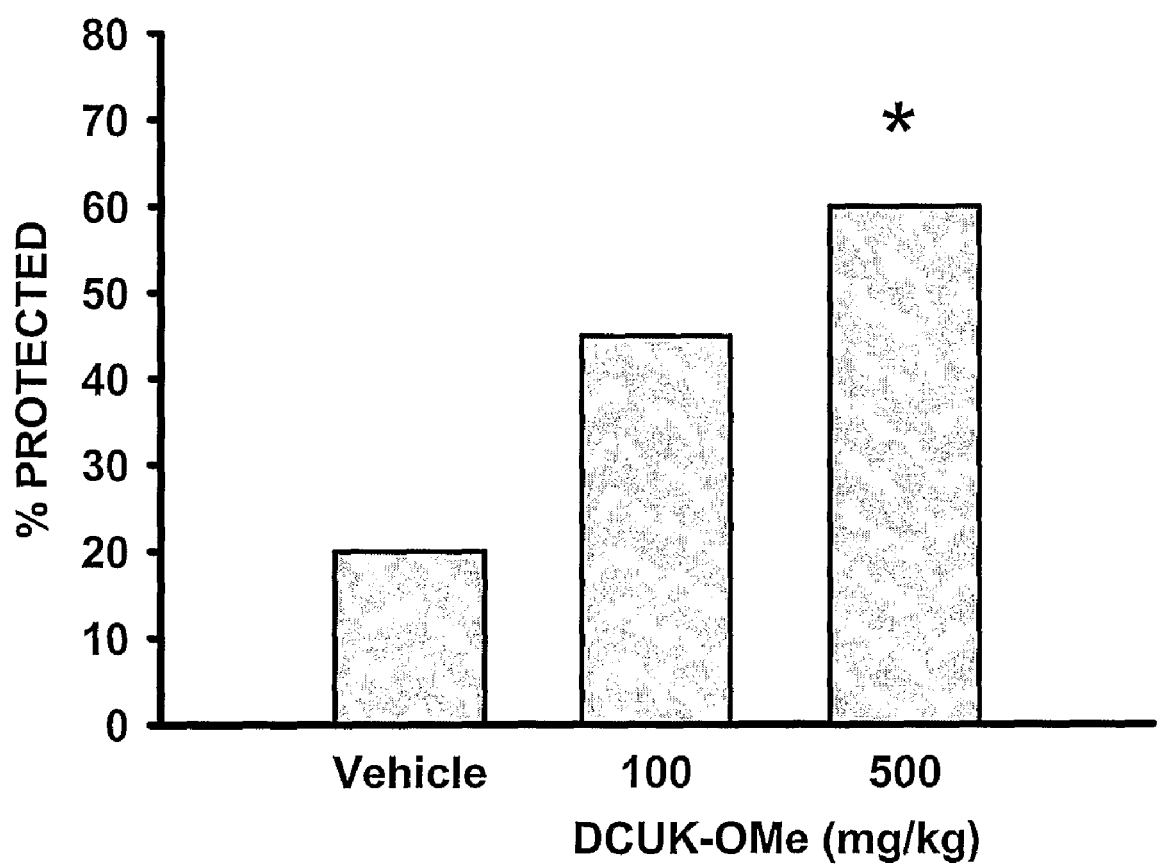
FIG. 11 illustrates protection against audiogenic seizures in DBA/2 mice following vehicle (n=20), 100 mg/kg DCUK-OMe (n=10), and 500 mg/kg DCUK-OMe (n=10). Data were analyzed by the Fisher's exact test. *P<0.05 compared with vehicle-injected mice.

FIG. 11 illustrates protection against audiogenic seizures in DBA/2 mice following vehicle (n=20), 100 mg/kg DCUK-OMe (n=10), and 500 mg/kg DCUK-OMe (n=10). Data were analyzed by the Fisher's exact test. *$P<0.05$ compared with vehicle-injected mice.

DETAILED METHODS

In Vitro Studies

Drugs. For all in vitro assays, stock solutions of DCUKA or DCUK-OMe were prepared fresh daily in dimethylsulfoxide (DMSO) then diluted into the incubation or bath solutions with sonication to the desired concentrations for experiments. Due to their limited solubility in aqueous buffers, DCUKA concentrations >300 µM and DCUK-OMe concentrations >100 µM could not be tested. In those assays where high ionic strength buffers were used, i.e., [$^3$H]batrachiotoxin (BTX) binding in depolarized synaptosomes, concentrations >50 µM could not be tested. The final concentration of DMSO in the assays ranged from 0.2 to 1%. In all assays, drug effects were compared with effects measured in the presence of the identical concentration of DMSO without drug.

Receptor Binding

General receptor-binding procedures. Male Sprague-Dawley rats were decapitated and their brains removed rapidly. The telencephalon (cerebral cortex, hippocampus, and striatum) was dissected and homogenized in 20 volumes of ice-cold 0.32 M sucrose, 20 mM HEPES-KOH (pH 7.2 at room temperature) containing protease inhibitors (10 mg/mL leupeptin, 5 mg/mL antipain, 20 mg/mL soybean trypsin inhibitor, 500 µM benzamidine, 10 mg/mL aprotinin, and 500 µM phenylmethylsulfonyl fluoride) with a motor driven glass-TEFLON® fluorocarbon homogenizer (8-10 strokes at setting 1). The homogenate was centrifuged at 800 g for 10 minutes. The pellet was discarded and the supernatant was centrifuged at 20,000 g for 20 minutes. The resulting pellet was resuspended in 20 volumes of distilled water containing 500 µM benzamidine and centrifuged for 20 minutes at 7500 g. Then the supernatant and buffy coat were centrifuged three times (51,500 g for 20 minutes) in the presence of distilled water containing 500 µM benzamidine. All centrifugation steps were carried out at 4° C. The final pellet was frozen rapidly at −80° C.

On the day of the assay, the pelleted membranes were resuspended in 20 volumes of 50 mM HEPES-KOH buffer, pH 7.4, and incubated for 20 minutes at 37° C. followed by centrifugation (51,500 g for 20 minutes). Membranes were then resuspended in 50 mM HEPES-KOH buffer (pH 7.8) containing 0.08% Triton X-100. After stirring for 30 minutes at 4° C., the membranes were pelleted by centrifugation (100,000 g for 20 minutes). The membranes were then washed twice by resuspension in the buffer appropriate for the binding assay and centrifugation (100,000 g for 20 minutes). The final pellet was suspended in assay buffer. The amount of protein in the final membrane preparation was determined with the bicinchoninic acid method (BCA; Pierce Chemical Co., Rockford, Ill.). The final protein concentration used for our studies was 300 to 600 µg/mL. Receptor-binding protocols described below were adapted from published procedures. For all assays, the samples, all in duplicate or triplicate, were placed into scintillation vials containing 5.5 mL of scintillation liquid (Ultima Gold; Packard Instrument Co., Inc., Meriden, Conn.) and the retained radioactivity was determined by conventional scintillation spectroscopy with a Beckman TA-6000 scintillation counter. Radio-ligands were purchased from DuPont-NEN (Boston, Mass.).

[$^3$H]5,7-Dichlorokynurenic acid (5,7-DCKA)-binding assay. The glycine recognition site of the NMDA receptor complex was labeled with the competitive antagonist [$^3$H]5,7-dichlorokynurenic acid (5,7-DCKA). Incubations were performed in 1 mL volume of 50 mM HEPES-KOH, pH 7.8, and 20 nM [$^3$H]5,7-DCKA. Incubations were for 45 minutes at 4° C. followed by termination by centrifugation. Nonspecific binding was defined with 1 mM glycine.

[$^3$H]BTX-binding assay. The alkaloid toxins veratridine, BTX, and aconitine, which cause persistent activation of sodium channels, bind to the neurotoxin receptor Site 2 associated with sodium channels. [$^3$H]BTX A 20-α-benzoate has been used to study the effects of anticonvulsant agents on the properties of VSNaCs in synaptosomal preparations of brain tissue. The crude $P_2$ synaptosomal pellet was obtained by homogenization and centrifugation through 0.32 M sucrose-5 mM $K_2HPO_4$. The pellet was resuspended in sodium-free assay buffer (50 mM HEPES, 5.4 mM KCl, 0.8 mM $MgSO_4$, 5.5 mM glucose, 130 mM choline chloride, pH 7.6) containing 1 µM tetrodotoxin and 1 µg/mL scorpion venom. [$^3$H] BTX binding was performed in 1 mL with 300 to 400 µg of tissue and 10 nM [$^3$H]BTX. Incubation was for 90 minutes at room temperature (21-23° C.) followed by vacuum filtration over GF/C filters. Nonspecific binding was defined with 0.3 mM veratridine. In some instances, binding assays were performed in synaptosomes under depolarizing conditions (130 mM KCl replacing choline chloride in buffer).

Data Analysis. The data were analyzed with SigmaPlot 5.0 and SigmaStat 2.0 (Jandel Scientific, Corte Madera, Calif.) software. In radioligand binding experiments, IC50 values were estimated from concentration-response curves by non-linear curve fitting to the three-parameter logistic equation, % Bound=Max/$\{1+([D]/IC_{50})^n\}$, where Max is the maximum amount of binding in the absence of drug, [D] is the concentration of drug, $IC_{50}$ is the estimated concentration of drug producing 50% inhibition of binding response, and n is the Hill slope.

NMDA Receptor Measurements in the *Xenopus* Oocyte Expression System

Following established procedures, mature female *Xenopus laevis* frogs were anesthetized by immersion for about 30 minutes in a 0.12% 3-aminobenzoic acid ethyl ester solution, a small incision was made in the abdominal wall and a piece of ovary was removed and placed in modified Barth's solution (MBS) [88 mM NaCl, 1 mM KCl, 10 mM HEPES, 0.82 mM $MgSO_4$, 2.4 mM $NaHCO_3$, 0.91 mM $CaCl_2$, 0.33 mM $Ca(NO_3)_2$, pH 7.5]. To facilitate manual dissection of oocytes, a section of ovary was transferred from MBS to a hypertonic buffer containing 108 mM NaCl, 2 mM KCl, 2 mM EDTA, 10 mM HEPES, pH 7.5, and theca and epithelial layers of mature oocytes (stages V and VI) were removed with surgical forceps. The follicular layer was removed by a 10-minute immersion in 0.5 mg/mL collagenase in buffer containing 83 mM NaCl, 2 mM KCl, 1 mM $MgCl_2$, and 5 mM HEPES. Human NR1a, NR2A, and NR2B cDNAs in pCDNA-1 Amp were transformed and amplified in XL-1 Blue cells (Stratagene, La Jolla, Calif.) and purified with the QIAFilter plasmid maxi kit (Qiagen, Inc., Chatsworth, Calif.).

Oocytes were injected with cDNA into the nucleus in the following concentrations: NR1a/2A cDNAs, 0.75 ng/30 nl 1:1 ratio and NR1a/2B cDNAs, 3.0 ng/30 nl 1:1 ratio. Injections were made with micropipettes (10-µm tip diameter) connected to a Drummond micropipettor attached to a micromanipulator. After injection, oocytes were individually placed in wells of 96-well microtiter plates containing incubation medium (MBS supplemented with 10 mg/l streptomycin, 10,000 U/l penicillin G, 50 mg/l gentamicin, 2 mM sodium pyruvate, 0.5 mM theophylline) that had been sterilized by passage through a 0.2-µm filter. Oocytes were incubated at 19° C. for 2 to 4 days after injection. Oocytes were then placed in a rectangular chamber (about 100 µl) and perfused (2 mL/min) with frog Ringer (115 mM NaCl, 2.5 mM KCl, 1.8 mM $CaCl_2$, 10 mM HEPES, pH 7.2). Oocytes were impaled with two glass electrodes (0.5-10 MΩ) filled with 3 M KCl and clamped at about 70 mV with a Warner Instruments (Hamden, Conn.) oocyte clamp (model OC-725C). A strip-chart recorder (Cole-Palmer Instrument, Vernon Hills, Ill.) continuously plotted the clamping currents. Agonist solutions with or without DCUKA were applied for 20 seconds at 5- to 10-minute intervals. Each oocyte represents a single n. Control responses to agonists (NMDA+ glycine) were always measured before and after DCUKA plus agonists response and averaged to account for run-down or run-up that normally occurs with glutamate receptors.

Patch Clamp Recordings of VSNaCs

Cell culture. The CNaIIA-1 cell line (gift of Dr. W. A. Catterall) was derived from a CHO-K1 cell line stably transfected with a cDNA encoding the rat brain type IIA $Na^+$ channel. CNaIIA-1 cells were cultured in RPMI medium (Gibco, Grand Island, N.Y.) with 5% fetal bovine serum, 100 µg/mL streptomycin, and 100 U/mL penicillin. G418 (400 µg/mL, Gibco) was included to select for transfectants. The cells were grown on the bottom of 25-cm$^2$ tissue culture flasks, and then passed and plated on pieces of glass cover slips in 35-mm dishes in a 5% CO2 atmosphere at 37° C. for 1-3 days before experimentation.

Whole-cell voltage-clamp recordings from CNaIIA cells. $Na^+$ currents were recorded using the whole-cell patch-clamp recording technique. The cultured cells on cover slips were transferred to a handmade recording chamber and continuously perfused at room temperature with extracellular solution containing (in mM): 130 NaCl, 4 KCl, 1.5 $CaCl_2$, 1.5 $MgCl_2$, 5 5lucose, 5 HEPES, 20 sucrose, pH 7.4, adjusted with NaOH. The recording chamber volume was approximately 0.4 mL and the flow rate was 0.6 mL/min. An MP-285 micromanipulator (Sutter Instrument Co., Novato, Calif.) was used to place the electrode onto the cell. Patch pipettes were pulled from borosilicate glass capillaries (Drummond Scientific Co., Broomall, Pa.) on an electrode puller (Model P-97, Sutter Instrument Co.) and were filled with a 0.2-µm-filtered internal solution containing (in mM): 90 CsF, 60 CsCl, 10 NaCl, 5 HEPES, pH 7.4, adjusted with NaOH. The pipettes had input resistance of 1-1.6 MΩ.

Recordings were performed at room temperature (22° C.) with an Axopatch 200A amplifier (Axon Instruments, Foster City, Calif.) and were filtered at 5 kHz. Leakage currents were subtracted using a P/4 or P/2 protocol. PClamp (Version 5.5, Axon Instruments) was used for experimental control and basic data analysis. Compensation circuitry was used to minimize series resistance errors and 90% of the series resistance was compensated. The series resistance before compensation was less than 2.5 MΩ, and except for only a few cells, most of the currents were less than 10 nA so that the uncompensated series resistance contributed less than a 2.5-mV error over all voltages studied. To minimize the contribution of the endogenous current (usually less than 90 pA), only cells with whole-cell maximal $Na^+$ currents of at least 1 nA were used in the analysis. Na⁺ currents recorded from cells always increased progressively within the first 20 minutes of establishing the whole-cell recording configuration and then were relatively stable for a further 20-40 minutes. Thus, drugs were applied only in this period.

Drugs and application. DCUKA was synthesized by Lohocla Research Corp. Carbamazepine (CBZ) was obtained from Sigma (St. Louis, Mo.). Stock solutions of 50 mM CBZ and DCUKA were prepared in dimethyl sulfoxide (DMSO) and then diluted into the bath solution to the desired concentrations for experiments. Sonication was necessary to solubilize DCUKA in DMSO. For all the experiments, the drugs were applied by perfusion. Control recordings showed that 0.2% dimethyl sulfoxide, the highest concentration used in any experiment, had no detectable effects on the Na⁺ currents in CNaIIA cells.

Data analysis. The data were analyzed using a combination of CLAMPFIT 6.0 (Axon Instruments) and SigmaPlot 4.0 (Jandel Scientific, Corte Madera, Calif.) software. The dose-response curve and Boltzman distributions were fit to the data points by using a nonlinear Marquardt-Levenberg algorithm. All results are presented as means±SEM.

Glutamate Excitotoxicity. Primary cultures of cerebellar granule cells were prepared from 7-day-old Sprague-Dawley rats. The cultures were maintained in plates containing 24 wells (volume of 1 mL/well). Culture density was about 1.5× $10^6$ cells/mL. Cell viability was assayed after 7 or 8 days in culture by the production of fluorescein, formed from fluorescein diacetate by esterases present in living cells. Cells were washed with magnesium ion-free Locke's buffer, and then exposed to 100 μM glutamate alone, glutamate and 10 μM glycine, or each of these conditions in the presence of 100 μM DCUKA or 100 μM DCUK-OMe at 25° C. for 30 minutes. DCUKA and DCUK-OMe were added in 2-μl aliquots to yield a final DMSO concentration of 0.2%. After glutamate/glycine±drug exposure, cells were washed twice with buffer and returned to conditioned medium for 24 hours before the fluorescein assay was performed. Fluorescence of each well was measured on a Perkin-Elmer HTS7000 plate reader (excitation 485 nm; emission 535 nm; 16 measurements per well) with optimal gain settings. For each 24-well plate, the fluorescence of one control culture well (i.e., not exposed to glutamate) was automatically set to the highest fluorescence value, and fluorescence values were determined in all other wells with the same gain settings. Fluorescence measurements in all 24 wells were normalized to the control culture and expressed as a percentage of this value. Data are expressed as percentage of cell death (100-percentage of control). Each individual measurement corresponds to the results for the contents of one culture well.

In Vivo Behavioral Studies

Drugs. For behavioral studies using intraperitoneal (i.p.) administration, DCUK-OEt was made up fresh daily in a 5% TWEEN 80/0.5% methylcellulose in 0.9% NaCl vehicle. For oral administration, DCUK-OEt was prepared as an emulsion. DCUK-OEt was added to canola oil to achieve a 2× concentration and stirred with sonication for 5 minutes to achieve a uniform suspension. An equal volume of a gelatin solution containing 1.2 g/L tartaric acid and 12% ethanol was added to the oil suspension and the resulting emulsion was stirred with sonication for an additional 5 minutes.

Subjects. Male C57BL/6 and DBA/2 mice were obtained from The Jackson Laboratory (Bar Harbor, Me.). Male Sprague-Dawley rats were purchased from Harlan. Mice were housed 10 per cage and rats 5 per cage under controlled environmental and lighting conditions (12-hour light/dark cycle; on at 9:00 AM) in an Association for Assessment of Laboratory Animal Care (AALAC)-accredited facility for at least 1 week, with food and water available ad libitum, before being used in experiments.

Pharmacokinetic Studies in Rats

Oral administration. Following overnight food deprivation, groups of 3 rats were administered 200 mg/kg DCUK-OEt by oral gavage (40 mg/mL DCUK-OEt at 5 mL/kg body weight). Groups of rats were anesthetized and sacrificed by decapitation at 0.25, 0.5, 1, 1.5, 2, 4, 6, and 8 hours post-administration. Trunk blood was collected into tubes containing $K_2$EDTA anticoagulant and brains were removed, washed thoroughly with 0.9% NaCl, and frozen on dry ice. Blood samples were centrifuged at 4000 rpm for 10 minutes. Plasma supernatant was removed and frozen at −80° C. until the time of the assay.

Liquid chromatographic-mass spectrometric determination of plasma and brain DCUKA and DCUK-OEt levels. Rat plasma sample preparation involved a simple protein precipitation procedure (100 μl plasma+250 μl acetonitrile containing 25 ng/mL of the internal standard, DCUK-OMe). After vortexing (5 minutes) and centrifugation (5000 g, 5 minutes, +4° C.), 200 μl of the supernatant was injected into the HPLC system and loaded onto the extraction column. Frozen brain tissue samples (about 0.5 g) were homogenized over liquid nitrogen using a mortar and pestle. The homogenized powder was transferred into the tubes containing 1.5 mL ice-cold 100% acetonitrile and 25 ng/mL DCUK-OMe (used as an internal standard). Following procedures were all performed on ice or at 4° C. The samples were further homogenized using an electric homogenizer for 30 seconds at 4° C. Subsequently, the tubes were placed into the ultrasonic bath for 30 minutes (on ice), and centrifuged afterwards at 1300 g for 10 minutes at 4° C. The supernatant was transferred into the HPLC tube. The pellet was re-extracted with 500 μL MeOH (containing 25 ng/mL DCUK-OMe), sonicated for 10 minutes, and centrifuged (10 minutes at 1300 g, 4° C.). The MeOH phase was combined with the acetonitrile solution from the first extraction step and 500 μL of the solution was directly injected into the HPLC system.

The two HPLC systems consisted of the following components (all series 1100, Agilent Technologies, Palo Alto, USA): HPLC I: G1312A binary pump, G1379A degasser; HPLC II: G1312A binary pump, and a G1316A column thermostat. A Sciex API 4000 triple-stage quadrupole mass spectrometer was used as detector (Applied Biosystems, Foster City, USA). The HPLC systems were connected via a 6-port column switching valve mounted on a step motor. The HPLC's switching valve and the mass spectrometer were controlled by the Analyst software (version 1.3.1., Applied Biosystems).

One hundred μL of the samples were injected onto a 4.6× 12.5 mm extraction column filled with Eclipse XDB-C8 material of 5 μm particle size (Agilent Technologies, Palo Alto, USA). Samples were washed with a mobile phase of 20% methanol and 80% 0.1% formic acid. The flow was about 3 mL/min. After 1 minute, the switching valve was activated and the analytes were back-flushed from the extraction column onto a 4.6×200 mm column filled with Eclipse XDB-C8 material of 5 μm particle size (analytical column). The mobile phase consisted of methanol and 0.1% formic acid. The flow rate was 1 mL/min. The gradient shown in Table 2 was used for the separation (A=methanol and B=0.1% formic acid).

TABLE 2

| Total Time(min) | Flow Rate(μl/min) | A (%) | B (%) |
|---|---|---|---|
| 0.0 | 1000 | 30.0 | 70.0 |
| 1.0 | 1000 | 30.0 | 70.0 |
| 2.0 | 1000 | 80.0 | 20.0 |
| 12.0 | 1000 | 98.0 | 2.0 |
| 13.0 | 1000 | 30.0 | 70.0 |
| 15.0 | 1000 | 30.0 | 70.0 |

The extraction column was cleaned with 98% methanol (flow: 5 mL/min) between minutes 1.1 and 12. The column switching valve was switched back into the extraction position after 12 minutes and then re-equilibrated to the starting conditions (minutes 13-15). Both columns were kept at room temperature. Injection of the next sample was initiated 15 min after injection of the previous sample.

The triple quadrupole mass spectrometer and HPLC system were interfaced with an atmospheric pressure chemical ionization spray source (APCI). Nitrogen (purity: 99.999%) was used as the Collision Activated Dissociation (CAD) gas. The mass spectrometer was run in the negative MRM (multiple reaction monitoring) mode. The declustering potential (DP) was set to 90 V and the entrance potential to −7 V (EP). The interface was heated to about 450° C. The first quadrupole was set to select the [M−H]$^+$ adducts of DCUKA (m/z 450.4), DCUK-OEt (m/z 478.3) and DCUK-OMe (IS, m/z 464.6). The second quadrupole was used as collision chamber, and the third quadrupole to select the characteristic product ions of DCUKA (m/z 237.0) and DCUK-OMe/DCUK-OEt (m/z 168.1). Peak area ratios obtained from MRM mode of the mass transitions for DCUKA (m/z 450.4→237.0), DCUK-OEt (m/z 478.3→168.1) and DCUK-OMe (IS, 464.6→168.1) were used for quantification.

Tactile and Thermal Hyperalgesia

Spinal Nerve Ligation and Sham Surgery. Anesthesia was maintained with 0.5% halothane in oxygen. After surgical preparation of the rats, a 2-cm paraspinal incision was made at the level L4-S2. The unilateral L5 and L6 spinal nerves were exposed and tightly ligated distal to the dorsal root ganglia by using 4-0 silk suture. The incisions were closed, and animals were allowed to recover. Sham-operated control rats were prepared in an identical manner without L5/L6 nerve ligation. Rats that exhibit motor deficiency (such as paw dragging or dropping) or fail to exhibit subsequent tactile hypersensitivity were excluded from the future testing (less than 5% of the animals were excluded). Separate groups of animals were used in tests for thermal and tactile hypersensitivity.

Tactile Hypersensitivity Test and Evaluation. Animals were placed in a suspended plastic chamber with a wire mesh platform and allowed to habituate for 15 minutes. Tactile hypersensitivity was determined by measuring paw withdrawal threshold in response to probing the plantar surface of the left hind paw with a series of 8 calibrated von Frey filaments (0.40, 0.70, 1.20, 2.00, 3.63, 5.50, 8.50, and 15.1 g). Measurements were taken before surgery and before and after administration of drug or vehicle. Withdrawal threshold was determined by sequentially increasing and decreasing stimulus intensity ("up and down" method), analyzed by using a Dixon nonparametric test, and expressed as the paw withdrawal threshold in gram force values. All studies were carried out 7 days after spinal nerve ligation (SNL).

Thermal Hypersensitivity Test (Radiant Heat Paw Withdrawal Test). Rats were placed in clear plastic chambers on a glass surface and were habituated for 15 minutes before testing. Thermal sensitivity was measured by using paw withdrawal latency to a radiant heat stimulus. A radiant heat source (i.e., infrared) was activated with a timer and focused onto the plantar surface of the left hind paw of a rat, and the latency to paw withdrawal was measured. A motion detector that halted both lamp and timer when the paw was withdrawn determined paw withdrawal latency. The latencies were measured before surgery and before and after drug or vehicle administration. A maximum cutoff of 33 seconds was used to prevent tissue damage. All studies were carried out 7 days after SNL.

Data Analysis. In all tests, baseline data were obtained for the spinal nerve-ligated and sham-operated groups before drug or vehicle administration. Within each treatment group, post-administration means were compared with the baseline values by analysis of variance, followed by post-hoc analysis of Fisher least significant difference test for multiple comparisons. A probability level of 0.05 indicates significance.

Anxiolytic Effects

The anxiolytic effect of the DCUK-OMe was tested in C57BL/6 mice with an elevated-plus maze apparatus. The plus-shaped maze consists of two arms that are open to the environment (30×5 cm) and two arms with side and end walls (30×5×15 cm). The arms are connected to a central area (5×5 cm) and the plus-maze is elevated from the floor to a height of 50 cm. All tests were conducted in a sound-attenuated room under low intensity light (50 lumens). Mice were allowed a 30-minutes habituation to the darkened testing room after which the mice were placed individually in the central area of the plus-maze facing one of the open arms, and were then allowed to move freely among the open and closed arms. A trained observer blind to the treatment conditions scored the number of entries into open arms and the number of entries into closed arms over a 5-minutes period. Between tests, the maze was wiped clean. The percentage of open arm entries (open arm entries/total arm entries) was calculated for each animal and used as a measure of the anxiolytic/anxiogenic effects of drug treatment. In addition, the total number of entries made into the center area was recorded as a measure of drug effects on locomotor activity. Mice were injected with vehicle (5% TWEEN 80/0.5% methylcellulose), 100 mg/kg DCUK-OMe, or 500 mg/kg DCUK-OMe about 90 minutes before testing in the plus-maze apparatus.

Audiogenic Seizures. Male DBA/2J mice (20-22 days old; 8-12 g) were used to evaluate the effects of DCUK-OMe in an animal model of partial seizures. Mice were dosed (i.p.) with vehicle (5% TWEEN 80/0.5% methylcellulose), 100 mg/kg DCUK-OMe, or 500 mg/kg DCUK-OMe, 30 minutes before noise stimulation. Mice were placed into a cylindrical Plexiglas testing chamber (15×50 cm, diameter 3 height) enclosed in a sound-attenuated box. After a 15- to 20-second habituation period, a high-intensity auditory stimulus (ringing doorbell; 12-16 kHz, 109 db) was activated for 30 seconds or until tonic hindlimb extension occurred. The seizure response in these mice is characterized by a progression of a wild running behavior, followed by loss of righting and clonus of the forelimbs, followed by tonic hindlimb extension, and finally respiratory arrest. The mice failing to exhibit clonic seizures were considered protected.

What is claimed is:

1. A method for the treatment of chronic neuropathic pain in a mammal comprising administering to a mammal suffering from chronic pain a pain relieving amount of a diarylureido-dihalokynurenate compound.

2. The method of claim 1 wherein the diarylureido-dihalokynurenate compound is a diarylureido-dihalokynurenate ester.

3. The method of claim 2 wherein the diarylureido-dihalokynurenate ester is an ester of an alcohol having 1 to 3 carbon atoms.

4. The method of claim 1 wherein the diarylureido-dihalokynurenate compound is a diphenylureido-dichlorokynurenate compound.

5. The method of claim 4 wherein the diphenylureido-dichlorokynurenate compound is an ester of an alcohol having 1 to 3 carbon atoms.

6. The method of claim 4 wherein the diphenylureido-dichlorokynurenate compound is an ethyl ester.

7. The method of claim 1 wherein the mammal is a human.

8. A method for the treatment of chronic neuropathic pain in a mammal comprising administering to a mammal suffering from chronic pain a pain relieving amount of a diarylureido-dihalokynurenate compound having the formula (I),

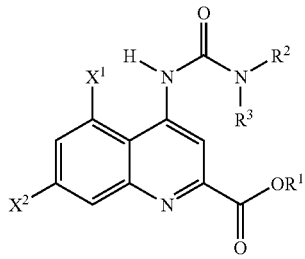

(I)

a tautomer thereof, or a pharmaceutically acceptable acid addition salt thereof;

wherein $R^1$ represents hydrogen, an alkyl group of 1 to 12 carbon atoms or a cycloalkyl group of 3 to 8 carbon atoms;

$R^2$ and $R^3$ each independently represent phenyl or phenyl having one or more alkoxy substituent; and $X^1$ and $X^2$ each independently represent a halogen substituent.

9. The method of claim 8 wherein $R^1$ is an alkyl group of 1 to 3 carbon atoms.

10. The method of claim 8 wherein $R^1$ is an ethyl group.

11. The method of claim 8 wherein $X^1$ and $X^2$ are each a chlorine substituent.

12. The method of claim 8 wherein the diarylureido-dihalokynurenate compound is selected from the group consisting of a N,N-diphenyl-4-ureido-5,7-dichloro-2-carboxyquinoline ester, a tautomer thereof, and an acid addition salt thereof.

13. The method of claim 8 wherein the diarylureido-dihalokynurenate compound is selected from the group consisting of N,N-diphenyl-4-ureido-5,7-dichloro-2-carboxyquinoline, N,N-diphenyl-4-ureido-5,7-dichloro-2-carboxy quinoline methyl ester, N,N-diphenyl-4-ureido-5,7-dichloro-2-carboxy quinoline ethyl ester, and a pharmaceutically acceptable acid addition salt thereof.

14. The method of claim 8 wherein the mammal is a human.

* * * * *